United States Patent
Houck

(10) Patent No.: US 10,912,925 B2
(45) Date of Patent: Feb. 9, 2021

(54) ASYMMETRIC CATHETER CURVE SHAPES

(71) Applicant: St. Jude Medical, Cardiology Division, Inc., St. Paul, MN (US)

(72) Inventor: Alexander Carson Houck, Hopkins, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 16/045,418

(22) Filed: Jul. 25, 2018

(65) Prior Publication Data

US 2018/0326183 A1    Nov. 15, 2018

Related U.S. Application Data

(63) Continuation of application No. 15/320,255, filed as application No. PCT/US2015/033999 on Jun. 3, 2015, now abandoned.

(60) Provisional application No. 62/013,392, filed on Jun. 17, 2014.

(51) Int. Cl.
| | |
|---|---|
| *A61M 25/01* | (2006.01) |
| *A61B 5/00* | (2006.01) |
| *A61B 5/042* | (2006.01) |
| *A61B 18/14* | (2006.01) |
| *A61M 25/00* | (2006.01) |
| *A61B 18/00* | (2006.01) |
| *A61N 1/05* | (2006.01) |

(52) U.S. Cl.
CPC ....... *A61M 25/0147* (2013.01); *A61B 5/0422* (2013.01); *A61B 5/6852* (2013.01); *A61B 18/1492* (2013.01); *A61M 25/00* (2013.01); *A61M 25/0009* (2013.01); *A61M 25/0043* (2013.01); *A61M 25/0105* (2013.01); *A61B 2018/00351* (2013.01); *A61B 2018/00577* (2013.01); *A61B 2018/00839* (2013.01); *A61M 25/0144* (2013.01); *A61M 2025/0046* (2013.01); *A61N 1/056* (2013.01)

(58) Field of Classification Search
CPC ...... A61B 18/1492; A61B 2017/00318; A61B 2017/00323; A61M 25/0147; A61M 25/0144; A61M 2025/015
USPC ...................................... 604/95.04
See application file for complete search history.

(56) References Cited

U.S. PATENT DOCUMENTS

| | | | | |
|---|---|---|---|---|
| 5,431,168 | A * | 7/1995 | Webster, Jr. | A61B 18/1492 600/435 |
| 6,926,669 | B1 * | 8/2005 | Stewart | A61B 18/1492 600/437 |
| 7,850,623 | B2 * | 12/2010 | Griffin | A61M 25/0013 600/585 |
| 2002/0161330 | A1 | 10/2002 | Nguyen | |
| 2002/0173785 | A1 | 11/2002 | Spear et al. | |

(Continued)

FOREIGN PATENT DOCUMENTS

| | | |
|---|---|---|
| WO | 2011033783 A1 | 3/2011 |
| WO | 2013169815 A1 | 11/2013 |

*Primary Examiner* — Deanna K Hall
(74) *Attorney, Agent, or Firm* — Dykema Gossett PLLC

(57) ABSTRACT

A deflectable catheter shaft with compression resistance coils configured to create different curve shapes when the catheter is steered or deflected in different directions. One or more compression resistance coils may include an elongated-pitch section. The compression resistance coils may be pull wire compression coils or body compression coils.

11 Claims, 9 Drawing Sheets

(56) References Cited

U.S. PATENT DOCUMENTS

| | | |
|---|---|---|
| 2010/0280525 A1* | 11/2010 | Alvarez .......... A61B 17/00234 |
| | | 606/130 |
| 2010/0331776 A1 | 12/2010 | Salahieh et al. |
| 2011/0054446 A1 | 3/2011 | Schultz |
| 2012/0078076 A1 | 3/2012 | Stewart et al. |
| 2012/0209143 A1 | 8/2012 | Schultz |
| 2013/0231657 A1 | 9/2013 | Datta et al. |
| 2013/0296781 A1 | 11/2013 | Tegg et al. |
| 2014/0135686 A1 | 5/2014 | Jimenez et al. |

\* cited by examiner

ASYMMETRIC CATHETER CURVE SHAPES

CROSS-REFERENCE TO RELATED APPLICATIONS

This application is a Continuation application of U.S. patent application No. 15/320,255, filed 19 Dec. 2016 (the '255 application); which is a National Stage Entry application of United States International patent application no. PCT/US2015/033999, filed 03 Jun. 2015 and published under International patent publication no. WO/2015/195339 on 23 Dec. 2015 (the '399 application). This application claims the benefit of United States provisional patent application no. 62/013,392, filed 17 Jun. 2014 (the '392 application). The '255 application; the '399 application; and the '392 application are hereby incorporated by reference as though fully set forth herein.

BACKGROUND

Field of the Disclosure

The instant disclosure relates generally to a deflectable catheter shaft, and particularly to a catheter shaft with compression resistance coils configured to create different curve shapes when the catheter is steered or deflected in different directions.

Background Art

Electrophysiology catheters are used in a variety of diagnostic, therapeutic, mapping, and ablation procedures to diagnose and/or correct conditions such as atrial arrhythmias, including, for example, ectopic atrial tachycardia, atrial fibrillation, and atrial flutter. Arrhythmias can create a variety of conditions including irregular heart rates, loss of synchronous atrioventricular contractions, and stasis of blood flow in a chamber of a heart, all of which can lead to a variety of symptomatic and asymptomatic ailments and even death.

Typically, a catheter is deployed and manipulated through a patient's vasculature to the intended site—for example, a site within a patient's heart or a chamber or vein thereof. The catheter carries one or more electrodes that can be used for cardiac mapping or diagnosis, ablation and/or other therapy delivery modes, or both, for example. Once at the intended site, treatment can include, for example, radio frequency (RF) ablation, cryoablation, laser ablation, chemical ablation, high-intensity focused ultrasound-based ablation, microwave ablation, and/or other ablation treatments. The catheter imparts ablative energy to cardiac tissue to create one or more lesions in the cardiac tissue and oftentimes a contiguous or linear and transmural lesion. This lesion disrupts undesirable cardiac activation pathways and thereby limits, corrals, or prevents errant conduction signals that can form the basis for arrhythmias.

To position a catheter within the body at a desired site, some type of navigation must be used, such as using mechanical steering features incorporated into the catheter (or a steerable or fixed-curve introducer sheath). In some examples, medical personnel may manually manipulate and/or operate the catheter using the mechanical steering features.

To facilitate the advancement of catheters through a patient's vasculature, the proximal end of the catheter can be manipulated to guide the catheter through a vessels and heart chambers. The simultaneous application of torque at the proximal end of the catheter and the ability to selectively deflect the distal tip of the catheter in a desired direction can permit medical personnel to adjust the direction of advancement of the distal end of the catheter and to position the distal portion of the catheter during an electrophysiological procedure. The distal tip can be deflected by one or more pull wires attached at the distal end of the catheter that extend proximally to a control handle, for example, that controls the application of tension on the pull wire or pull wires.

Two of the mechanical considerations for a catheter shaft are that it transmit torque and resist compression during use. With respect to transmitting torque, medical personnel normally navigate the distal end of the catheter to a desired location in part by manipulating a handle disposed at the proximal end of the catheter shaft, or by rolling the proximal portion of the catheter shaft about its longitudinal axis with their fingers. Substantial frictional forces sometimes resist transmission of torque down the length of the catheter. With respect to resisting compression during use, catheter shafts may include compression coils that comprise a plurality of stacked coils, such that the catheter shaft may be laterally deflected or curved while resisting longitudinal compression and the concomitant problems that such longitudinal compression may cause.

The foregoing discussion is intended only to illustrate the present field and should not be taken as a disavowal of claim scope.

BRIEF SUMMARY

Embodiments of the present disclosure include a deflectable catheter shaft with compression resistance coils configured to create different curve shapes when the catheter is steered or deflected in different directions. One or more compression resistance coils may include an elongated-pitch section. The compression resistance coils may be pull wire compression coils or body compression coils.

In accordance with an aspect of the present disclosure a steerable catheter comprises a proximal catheter shaft section comprising a proximal end and a distal end; a distal deflectable section adjacent to the distal end of the proximal catheter shaft section, the distal deflectable section comprising a proximal end and a distal end; a first compression coil surrounding a first pull wire and extending longitudinally through the proximal catheter shaft section from the proximal end of the proximal catheter shaft section to the proximal end of the distal deflectable section; and a second compression coil surrounding a second pull wire and extending longitudinally, parallel to the first compression coil, through the proximal catheter shaft section from the proximal end of the proximal catheter shaft section to the proximal end of the distal deflectable section; wherein the first compression coil comprises a first distal elongated-pitch section.

In accordance with another aspect of the present disclosure a steerable catheter comprises a proximal catheter shaft section comprising a proximal end, a distal end, and a central lumen; a distal deflectable section adjacent to the distal end of the proximal catheter shaft section, the distal deflectable section comprising a proximal end and a distal end; a body compression coil surrounded by the proximal catheter shaft section and extending longitudinally through the central lumen from the proximal end of the proximal catheter shaft section to a first region at the proximal end of the distal deflectable section; a first pull wire extending longitudinally through the body compression coil from the proximal end of the proximal catheter shaft section to a second region at the proximal end of the distal deflectable section, the second region being distal to the first region; a second pull wire extending longitudinally, parallel to the first pull wire, through the body compression coil from the proximal end of the proximal catheter shaft section to the second region at the proximal end of the distal deflectable section; and a pull wire compression coil surrounding the first pull wire within the body compression coil, the pull wire compression coil extending longitudinally from the proximal end of the proximal catheter shaft section to the second region at the proximal end of the distal deflectable section.

In accordance with another aspect of the present disclosure a steerable catheter comprises a proximal catheter shaft section comprising a proximal end and a distal end; a distal deflectable section adjacent to the distal end of the proximal catheter shaft section, the distal deflectable section comprising a proximal end and a distal end; a compression coil surrounding a pull wire and extending longitudinally through the proximal catheter shaft section from the proximal end of the proximal catheter shaft section to the proximal end of the distal deflectable section; and wherein the compression coil comprises a distal elongated-pitch section.

The foregoing and other aspects, features, details, utilities, and advantages of the present disclosure will be apparent from reading the following description and claims, and from reviewing the accompanying drawings.

DETAILED DESCRIPTION

Figure 1:
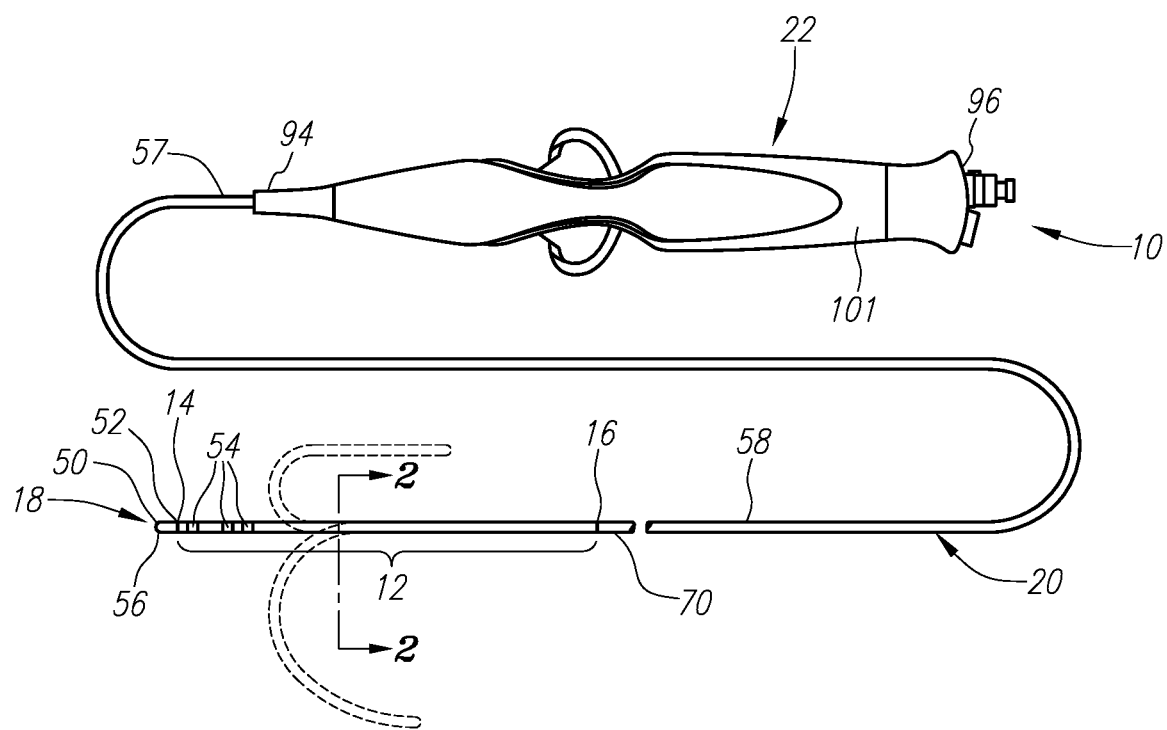
FIG. 1 is a schematic view of a catheter incorporating a deflectable catheter shaft section in accordance with an embodiment of the disclosure.

FIG. 1 generally illustrates a deflectable electrophysiology catheter 10 that comprises a deflectable catheter shaft section or distal deflectable section 12 in accordance with an embodiment of the disclosure. Deflectable catheter shaft section 12 comprises an elongated body having a distal end 14 and a proximal end 16. In its most general form, catheter 10 further comprises a tip assembly 18 located at the distal end 14 of the deflectable catheter shaft section 12, a proximal catheter shaft section 20 (including a proximal end 57 and a distal end 58) located proximal to the proximal end 16 of the deflectable catheter shaft section 12, and a handle assembly 22. Deflectable catheter shaft section 12 and proximal catheter shaft section 20 can be made of polytetrafluoroethylene (PTFE) and may comprise, for example, a PTFE sleeve 60 (see FIGS. 2 and 4). Deflectable catheter shaft section 12 can also include one or more electrodes, such as ring electrodes 54 and tip electrode 56, for example. Catheter 10 may be used in any number of diagnostic and therapeutic applications, such as the recording of electrograms in the heart, the performance of a cardiac ablation procedure, and other similar applications/procedures.

Still referring to FIG. 1, deflectable catheter shaft section 12 is disposed between the tip assembly 18 and the proximal catheter shaft section 20. The length and diameter of the deflectable catheter shaft section 12 can vary according to the application. Generally, the length of the deflectable catheter shaft section 12 can range from about 2 inches (50.8 mm) to about 6 inches (152.4 mm) and the diameter of the deflectable catheter shaft section 12 can range from about 5 French to about 12 French. The diameter of the deflectable catheter shaft section 12 can be about 7 French in accordance with some embodiments of the disclosure. Although these particular dimensions are mentioned in particular, the dimensions of the deflectable catheter shaft section 12 can vary in accordance with various applications of the deflectable catheter shaft section 12. The deflectable catheter shaft section 12 can be configured for deflection independent of, or substantially independent of, the proximal catheter shaft section 20.

Figure 2:
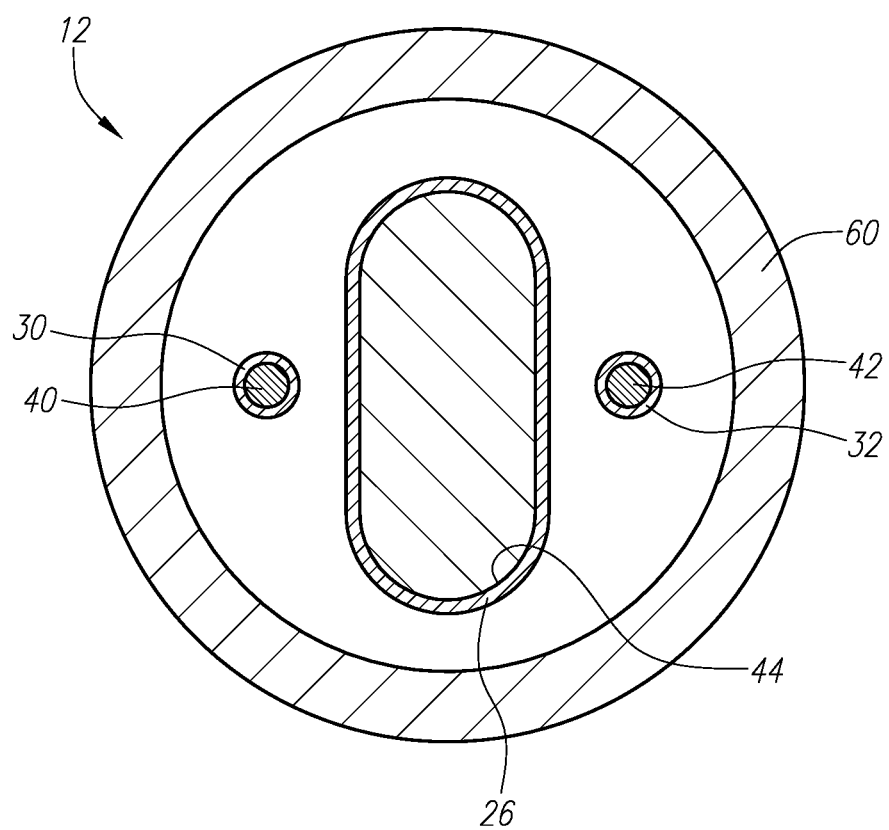
FIG. 2 is a schematic cross-sectional view of the deflectable catheter shaft section of FIG. 1 taken along line 2-2 in FIG. 1, with various components of the catheter omitted for clarity.

FIG. 2 illustrates a schematic cross-sectional view of the deflectable catheter shaft section 12 taken along line 2-2, as shown in FIG. 1. In the illustrated embodiment, the deflectable catheter shaft section 12 comprises three substantially separate tubes 26, 30, and 32 forming lumens, each extending along the longitudinal axis of deflectable catheter shaft section 12. In another embodiment, deflectable catheter shaft section 12 may include fewer or more than three lumens. The lumens of tubes 26, 30, and 32 may extend along the entire length of deflectable catheter shaft section 12 or less than the entire length of deflectable catheter shaft section 12. Each lumen of tubes 26, 30, 32 may be formed to have a predetermined cross-sectional profile and shape. Each lumen of tubes 26, 30, 32 may be lined with liners (not shown), which may be attached to an inner surface of tubes 26, 30, or 32, such as the inner surface 44 of tube 26, for example. The liners may serve the purpose of providing a lubricious surface (e.g., to allow for the sliding of the pull wires) and insulating the components within the lumens of tubes 26, 30, 32. If provided, the liners may be constructed of a polymeric material, such as polytetraflouroethylene (PTFE) or any other suitable material. In an embodiment, the PTFE lining is 0.002 inches thick and has no impact or minimal impact on the deflection curve of deflectable catheter shaft section 12.

The lumen of tube 26 may be configured to house wiring for electrodes or for other electrical components. The lumen of tube 26 may also be configured for use as an irrigation fluid passageway and the like. The lumens of tubes 30 and 32, which may be located parallel to and on opposite lateral sides of deflectable catheter shaft section 12, may be configured to house pull wires 40 and 42, respectively, to enable the deflectable catheter shaft section 12 to deflect in two or more directions. In particular, the handle assembly 22 may comprise at least one pull wire operatively connected to it to facilitate deflection of the deflectable catheter shaft section 12. The pull wires 40, 42 may be formed from a stainless steel (e.g., grades 304 or 316), alloy 35N LT, superelastic nickel-titanium (known as NiTi or Nitinol) wire, carbon fiber, para-aramid synthetic fiber generally available from DuPont under the brand name KEVLAR®, or other suitable material in accordance with various embodiments of the disclosure.

Figure 3:
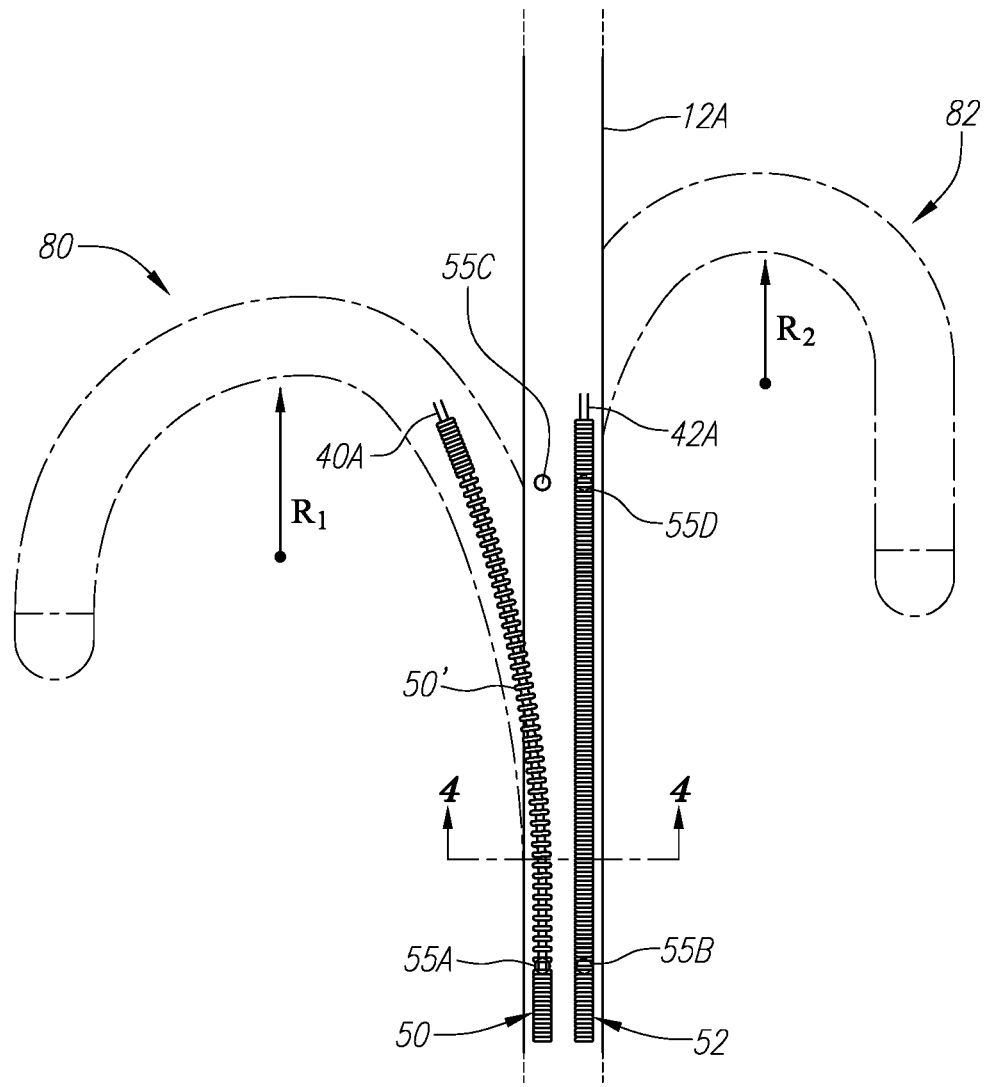
FIG. 3 is a schematic side view of a distal catheter shaft section showing two pull wire compression coils, one with an elongated pitch section, and showing (in phantom) two possible curve shapes of the distal catheter shaft section.

FIG. 3 depicts in solid lines a portion of deflectable catheter shaft section 12A in an undeflected configuration, and depicts in phantom lines two curved configurations 80, 82 of the deflectable catheter shaft section when it is fully deflected in opposite directions. The proximal end of deflectable catheter shaft section 12A can include two compression coils 50 and 52 surrounding pull wires 40A and 42A, respectively. The term "compression coils," as used herein, means an elongated pull-wire coil comprising (a) at least one longitudinal-compression-resistant section, including adjacent coils that are touching, and also possibly comprising (b) one or more elongated-pitch sections, each elongated-pitch section including non-touching adjacent coils.

Compression coils 50 and 52 may be identical in length and parallel to one another. In an example, compression coils 50 and 52 can be made of grade 304 stainless steel rolled flat wire that is about 0.008 inches by 0.005 inches. The inner diameter of compression coils 50 and 52 can be about 0.01 inches and the outer diameter of compression coils 50 and 52 can be about 0.02 inches, for example. Compression coil 50, which is associated with deflection curve 80, can include a distal elongated-pitch section 50'. Compression coil 50 can be attached to the sidewall that also comprises part of deflectable catheter shaft section 12A at location 55A via RF bonding, glue, sonic welding, or thermal welding, for example. In an embodiment, though not shown in FIG. 3, compression coil 50 can optionally be attached to the sidewall that also comprises part of deflectable catheter shaft section 12A at location 55C via similar attachment means. Compression coil 52 is associated with deflection curve 82. Compression coil 52 can be attached to the sidewall that also comprises part of deflectable catheter shaft section 12A at location 55D and at location 55B via RF bonding, glue, sonic welding, or thermal welding, for example.

Deflection curve 80 has a radius R1, and deflection curve 82 has a radius R2. In this embodiment, R1 is greater than R2, resulting in asymmetric curve shapes of the deflectable catheter shaft section 12A. When pull wire 42A experiences a longitudinal load (i.e., gets pulled proximally), the deflectable catheter shaft section 12A begins to form the proximal portion of deflection curve 82 near the distal end of compression coil 52, such as between location 55D and the distal end of compression coil 52. In contrast, when pull wire 40A experiences a longitudinal load, compression coil 50 allows the deflectable catheter shaft section 12A to begin to form the proximal portion of deflection curve 80 near location 55A, adjacent to the proximal end of compression coil 50. The elongated-pitch section 50' of compression coil 50 permits the deflectable catheter shaft section 12A to begin curving from a more proximal location than does compression coil 52 (e.g., location 55A versus location 55D).

Figure 4:
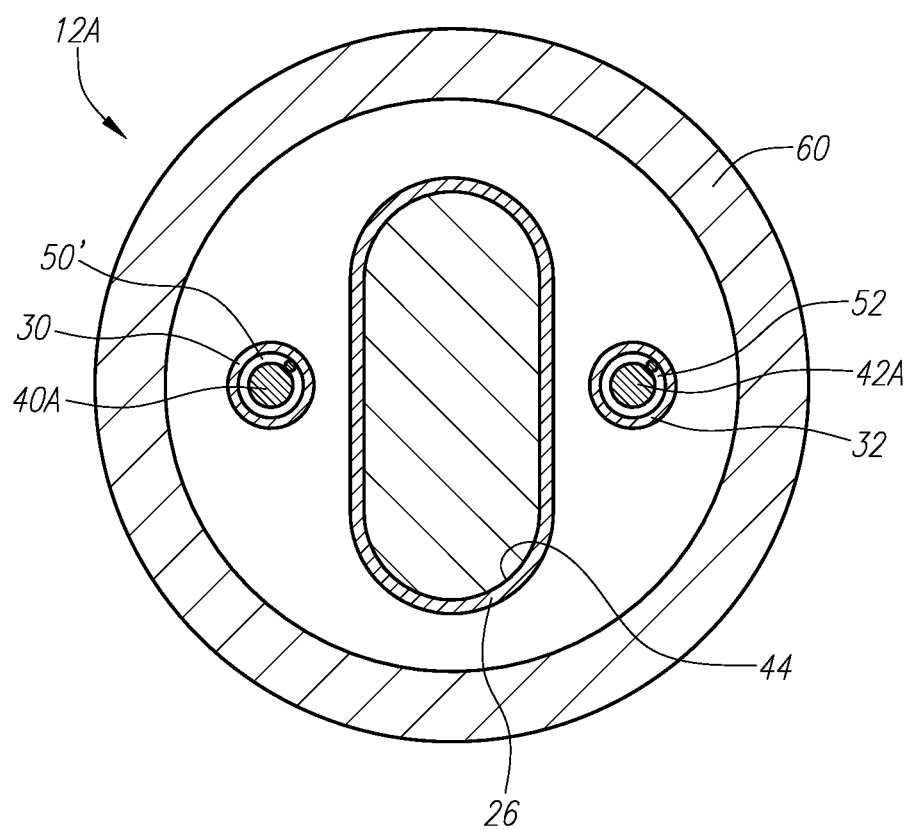
FIG. 4 is a schematic cross-sectional view of the proximal catheter shaft section of FIG. 3 taken along line 4-4 in FIG. 3, with various components of the catheter omitted for clarity.

FIG. 4 illustrates a schematic cross-sectional view of the proximal end of the deflectable catheter shaft section 12A taken along line 4-4, as shown in FIG. 3. Lumens formed by tubes 26, 30, and 32 are similar to those described above with respect to FIG. 2. In addition, compression coil 52 is shown surrounding pull wire 42A, and compression coil 50' is shown surrounding pull wire 40A.

Figure 5:
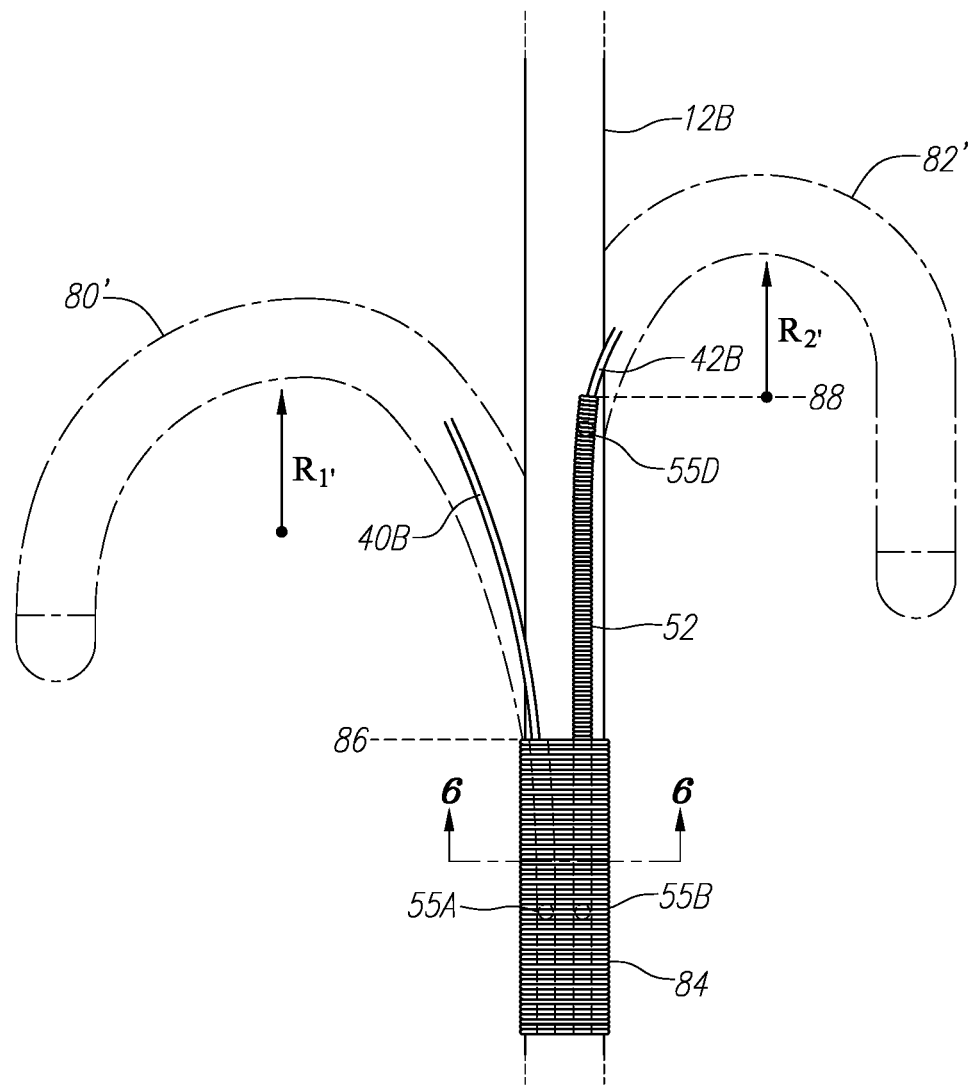
FIG. 5 is a schematic side view of a distal catheter shaft section showing one pull wire compression coil and a body coil, and showing (in phantom) two possible curve shapes of the distal catheter shaft section.

FIG. 5 illustrates a portion of a deflectable catheter shaft section 12B and its deflection curves 80' and 82' in another embodiment of the present disclosure. In this embodiment, a body compression coil 84 is surrounded by the PTFE 60 (not shown in FIG. 5) that may form at least the outer material of the deflectable catheter shaft section 12B. Body coil 84 encompasses the internal contents of the proximal portion of the deflectable catheter shaft section 12B. In addition to body coil 84, the present embodiment can include compression coil 52 surrounding pull wire 42B. No compression coil surrounds pull wire 40B in this embodiment. Body coil 84 can be attached to the sidewall that also comprises part of deflectable catheter shaft section 12B at location 55A and/or 55B via RF bonding, glue, sonic welding, or thermal welding, for example. Compression coil 52 can be attached to the sidewall that also comprises part of deflectable catheter shaft section 12B at location 55D and, optionally, at location 55B via RF bonding, glue, sonic welding, or thermal welding, for example.

Deflection curve 80' has a radius R1', and deflection curve 82' has a radius R2'. In this embodiment, R1' is greater than R2', resulting in asymmetric curve shapes of the deflectable catheter shaft section 12B. When pull wire 42B experiences a longitudinal load, the deflectable catheter shaft section 12B begins to form the proximal portion of deflection curve 82' near the distal end of compression coil 52, such as between location 55D and the distal end of compression coil 52 marked by line 88. In contrast, when pull wire 40B experiences a longitudinal load, body coil 84 allows the deflectable catheter shaft section 12B to begin to form the proximal portion of deflection curve 80' near line 86 at the distal end of body coil 84. The compression coil 52, in addition to body coil 84, causes the deflectable catheter shaft section 12B to begin curving from a more distal location than does body coil 84 alone (e.g., line 88 vs line 86).

Figure 6:
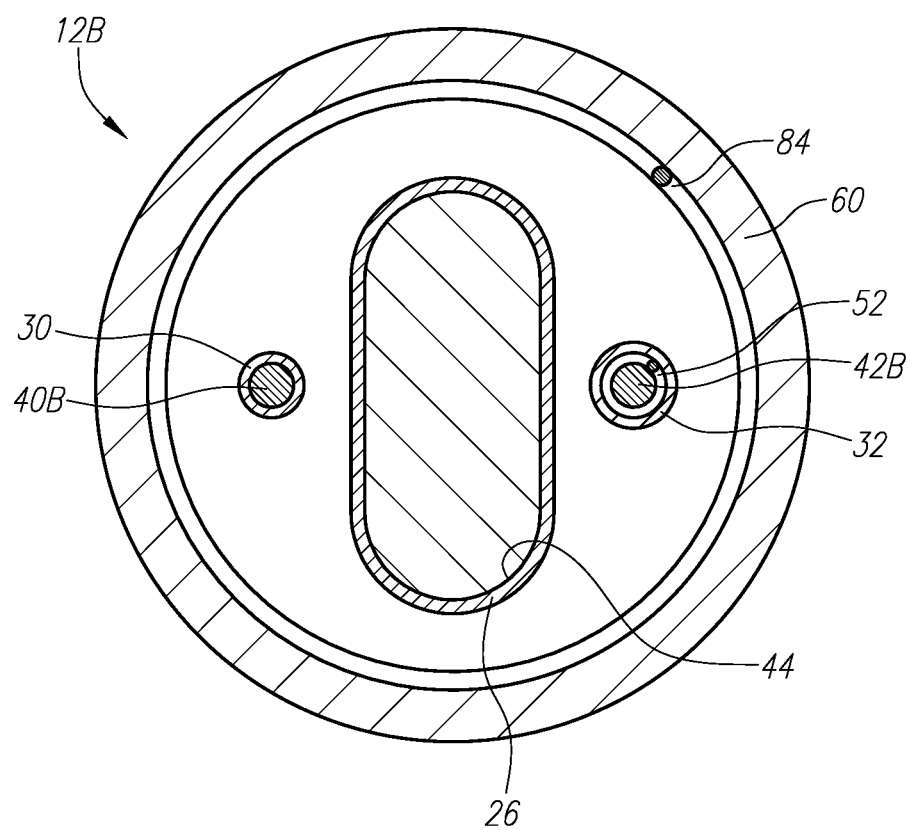
FIG. 6 is a schematic cross-sectional view of the proximal catheter shaft section of FIG. 5 taken along line 6-6 in FIG. 5, with various components of the catheter omitted for clarity.

FIG. 6 illustrates a schematic cross-sectional view of the proximal end of the deflectable catheter shaft section 12B taken along line 6-6, as shown in FIG. 5. Lumens formed by tubes 26, 30, and 32 are similar to those described above with respect to FIG. 2. In addition, compression coil 52 is shown surrounding pull wire 42B, and body coil 84 is shown surrounding the internal contents of the proximal portion of the deflectable catheter shaft section 12.

Figure 7:
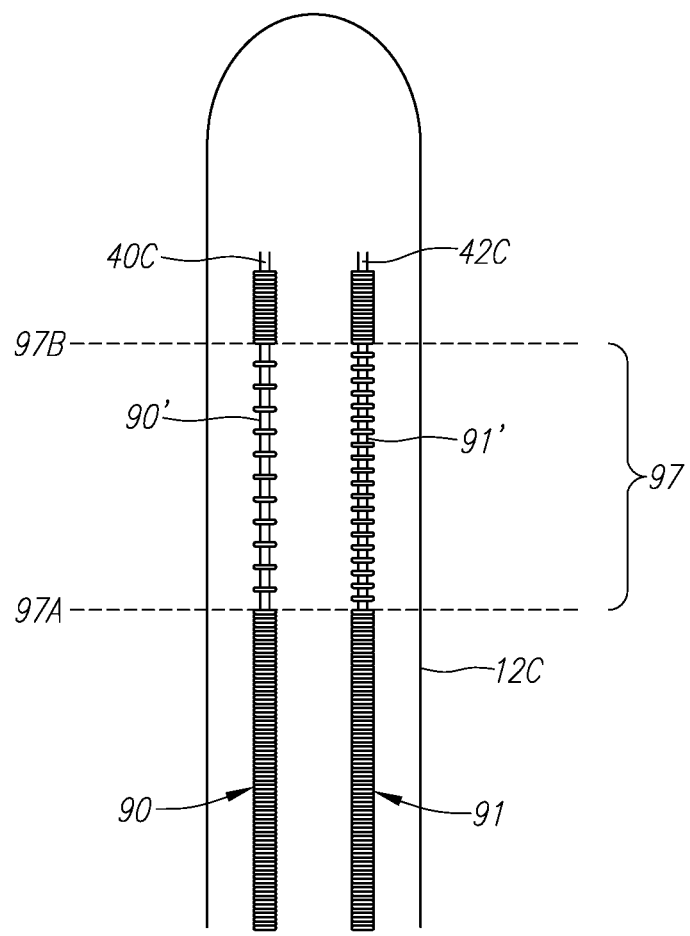
FIG. 7 is a schematic, fragmentary side view of a catheter showing two pull wire compression coils, each with a different elongated-pitch section in the elongated-pitch zone.

FIG. 7 is a side view of a deflectable catheter shaft section 12C showing two pull wire compression coils 90 and 91 surrounding pull wires 40C and 42C, respectively. Compression coils 90 and 91 may be identical in length and parallel to one another. In this embodiment, both compression coils 90 and 91 have elongated-pitch sections, 90' and 91', respectively, located in an elongated-pitch zone 97. Elongated-pitch zone 97 can have a proximal end 97A and a distal end 97B. Elongated-pitch section 90' is more elongated, or more stretched out, than elongated-pitch section 91' in FIG. 7. Consequently, when pull wire 40C experiences a longitudinal load, the curve of deflectable catheter shaft section 12C (not shown) may have a larger radius than when pull wire 42C experiences a longitudinal load.

Extrapolating from the example shown in FIG. 7, any combination of elongated-pitch sections of any pitch size can be substituted for 90' or 91', thereby creating a plurality of different curve shapes and curve-shape combinations for a given catheter. This can be beneficial for creating many different asymmetric or symmetric catheter curve shapes that can be used in a variety of medical procedures and/or with a variety of different anatomies.

Figure 8:
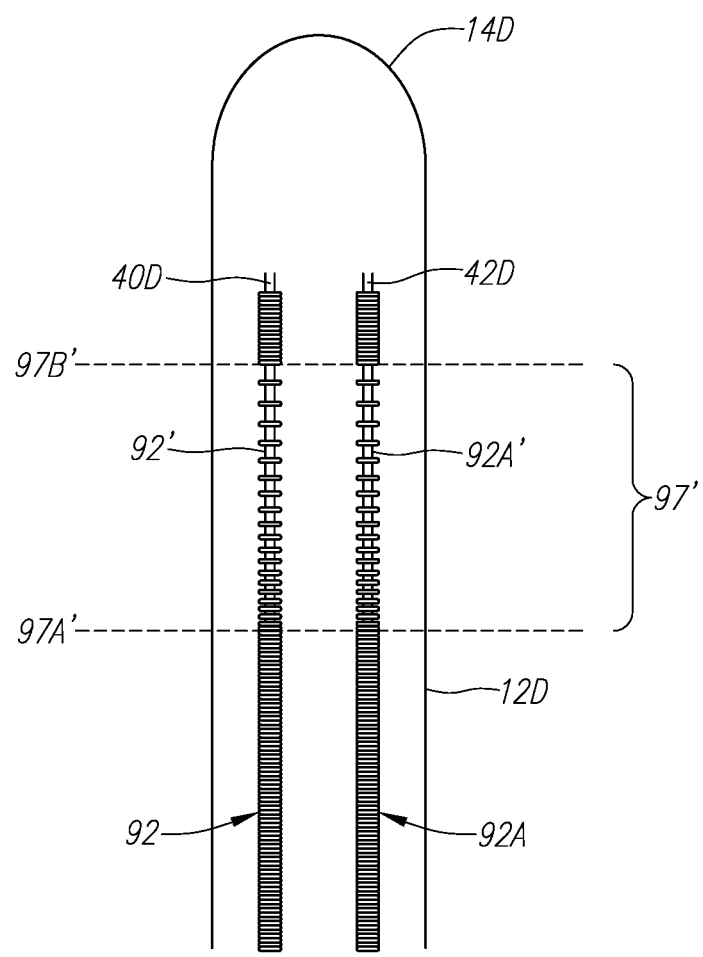
FIG. 8 is a schematic, fragmentary side view of a catheter showing two pull wire compression coils, both with a variable pitch in the elongated-pitch zone.

FIG. 8 is a side view of a deflectable catheter shaft section 12D showing two pull wire compression coils 92 and 92A surrounding pull wires 40D and 42D, respectively. Compression coils 92 and 92A may be identical in length and parallel to one another. In this embodiment, both compression coils 92 and 92A have elongated-pitch sections, 92' and 92A', respectively, located in an elongated-pitch zone 97'. Elongated-pitch zone 97' includes a proximal end 97'A and a distal end 97'B. Elongated-pitch sections 92' and 92A', which can be identical, have a variable pitch. The variable pitch in this embodiment is a gradually elongating pitch moving from the proximal end 97'A to the distal end 97'B of the elongated-pitch zone 97'. The gradually elongating pitch can cause deflectable catheter shaft section 12D to display symmetric curve shapes upon bending, with increased flexibility toward the distal end 14D of deflectable catheter shaft section 12D. In an embodiment, the durometer of the material (e.g. PTFE) forming deflectable catheter shaft section 12D can be uniform throughout the length of deflectable catheter shaft section 12D (rather than gradually decreasing toward the distal end 14D) because the gradual elongation of elongated-pitch sections 92' and 92A' can provide the required flexibility of deflectable catheter shaft section 12D. This can provide advantages in terms of the cost and ease of manufacturing such catheter shafts.

Figure 9:
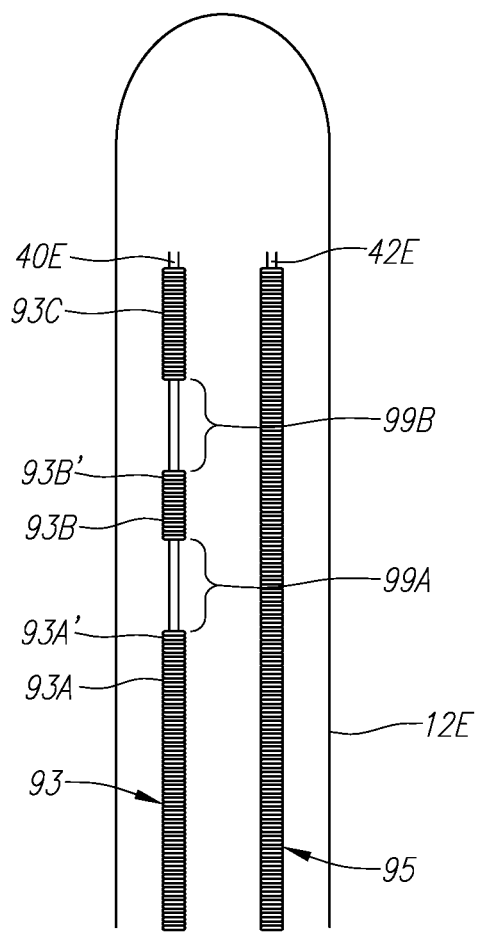
FIG. 9 is a schematic, fragmentary side view of a catheter showing two pull wire compression coils, one of which is discontinuous.

FIG. 9 is a side view of a deflectable catheter shaft section 12E showing two pull wire compression coils 93 and 95 surrounding pull wires 40E and 42E, respectively. Compression coils 93 and 95 may be identical in overall length and parallel to one another. In this embodiment, compression coil 93 includes three sections 93A, 93B, and 93C, separated by two breaks, 99A and 99B, respectively. This can cause deflectable catheter shaft section 12E to form a complex curve with bends in two locations. When pull wire 40E experiences a longitudinal load, deflectable catheter shaft section 12E can form a first bend at or near the distal end 93A' of section 93A. Similarly, when pull wire 40 E experiences a longitudinal load, deflectable catheter shaft section 12E can form a second bend at or near the distal end 93B' of section 93B. This can result in deflectable catheter shaft section 12E being capable of forming asymmetric curve shapes, one of which is a complex curve.

Although embodiments of a catheter shaft with compression coils have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Various embodiments have been described above to various apparatuses, systems, and/or methods. Numerous specific details have been set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated above are non-limiting examples, and thus it can be appreciated that the specific structural and functional details disclosed above may be representative and do not necessarily limit the scope of the embodiments, the scope of which is defined solely by the appended claims.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" have been used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" have been used above with respect to the illustrated embodiments. However, surgical instruments may be used in many orientations and positions, and these terms are not intended to be limiting and absolute.

What is claimed is:

1. A steerable catheter comprising
   a proximal catheter shaft section comprising a proximal end and a distal end;

a distal deflectable section adjacent to the distal end of the proximal catheter shaft section the distal deflectable section comprising a proximal end and a distal end;

a first compression coil surrounding a first pull wire and extending longitudinally through the proximal catheter shaft section from the proximal end of the proximal catheter shaft section to the proximal end of the distal deflectable section, the first compression coil comprising a first distal elongated-pitch section having an elongated pitch with respect to a pitch of a proximal section of the first compression coil, and a second compression coil surrounding a second pull wire and extending longitudinally, parallel to the first compression coil, through the proximal catheter shaft section from the proximal end of the proximal catheter shaft section to the proximal end of the distal deflectable section;

wherein the first distal elongated-pitch section comprises a proximal end and a distal end;

wherein the first compression coil is secured within the proximal catheter shaft section at least at a first location, the first location being at or near the proximal end of the first distal elongated-pitch section;

wherein the second compression coil is secured within the proximal catheter shaft section at least at a second location; and wherein the first location and the second location lie within a cross-sectional plane, the cross-sectional plane being perpendicular to a longitudinal axis of the catheter.

2. The steerable catheter of claim 1, wherein the first distal elongated-pitch section is about 0.25-1.0 inches (6.35-25.4 mm) in length.

3. The steerable catheter of claim 1, wherein the first and second compression coils are secured within the proximal catheter shaft section via at least one of RF bonding, glue, sonic welding, or thermal welding.

4. The steerable catheter of claim 1, wherein at least one of the first compression coil or the second compression coil comprises two or more discontinuous sections.

5. The steerable catheter of claim 1, wherein the second compression coil comprises a second distal elongated-pitch section.

6. The steerable catheter of claim 5, wherein the second distal elongated-pitch section comprises a variable pitch;

wherein the second distal elongated-pitch section comprises a proximal end and a distal end;

and wherein the variable pitch comprises a progressively elongating pitch longer from the proximal end of the second distal elongated-pitch section to the distal end of the second distal elongated-pitch section.

7. The steerable catheter of claim 1, further comprising a body compression coil surrounded by the proximal catheter shaft section and extending longitudinally through a central lumen from the proximal end of the proximal catheter shaft section to a first region at the proximal end of the distal deflectable section.

8. The steerable catheter of claim 1, further comprising a sleeve surrounding the proximal catheter shaft section, wherein the sleeve comprises a material that forms the proximal catheter shaft section.

9. The steerable catheter of claim 8, wherein the material includes PTFE.

10. The steerable catheter of claim 1, wherein the first compression coil and the second compression coil are of equal length.

11. The steerable catheter of claim 1, wherein when the catheter is deflected toward the first pull wire, the catheter forms a first curve with a first radius;

wherein, when the catheter is deflected toward the second pull wire, the catheter forms a second curve with a second radius; and wherein the first radius is greater than the second radius.

* * * * *